United States Patent [19]

Hüsler et al.

[11] Patent Number: 5,008,302
[45] Date of Patent: Apr. 16, 1991

[54] TITANOCENES, THE USE THEREOF, AND N-SUBSTITUTED PYRROLES

[75] Inventors: Rinaldo Hüsler, Marly, Switzerland; Bernd Klingert, Inzlingen, Fed. Rep. of Germany; Manfred Rembold, Aesch; Eginhard Steiner, Füllinsdorf, both of Switzerland

[73] Assignee: Ciga-Geigy Corporation, Ardsley, N.Y.

[21] Appl. No.: 273,522

[22] Filed: Nov. 21, 1988

[30] Foreign Application Priority Data

Dec. 1, 1987 [CH] Switzerland ............... 4683/87

[51] Int. Cl.$^5$ ............... B01J 31/00; C08F 2/50; C08F 4/76; C07D 207/00
[52] U.S. Cl. ............... 522/14; 430/920; 430/947; 430/281; 548/402; 502/162; 502/5; 522/26; 522/63
[58] Field of Search ............... 430/920, 947, 281; 548/402; 522/63, 14, 26; 502/162, 5

[56] References Cited

U.S. PATENT DOCUMENTS 4,590,287 5/1986 Riediker et al. ............... 556/53

OTHER PUBLICATIONS

M. A. Chaudhari, et al., J. Organometal. Chem., 2, 206(1964).
C. Yamborski, et al., J. Organometal. Chem. 4, 446 (1965).
U. Jaeger, et al., Chem. Ber. 119, 3405 (1986).
D. Barton, et al., "Comprehensive Organic Chemistry", vol. 4, Pergamon Press, Oxford pp. 296-300.
H. Kofod, et al., J. Chem. Soc. 1952, 1467.
G. Stefancich, et al., Farmaci-Ed. Sc., 40, 237 (1985).
Houben-Weyl, vol. VI/3, 730-731 (1965).
D. Barton, et al., "Comprehensive Organic Chemistry", vol. 4, Pergamon Press, Oxford pp. 458-463.
Houben-Weyl, vol. IV/1d, 257-258 (1981).
H. G. Dunlop, et al., J. Chem. Soc. 1939, 1945.

Primary Examiner—Cynthia Hamilton
Attorney, Agent, or Firm—Luther A. R. Hall

[57] ABSTRACT

Titanocenes containing two 5-membered cyclodienyl groups, for example cyclopentadienyl, and one or two 6-membered carbocyclic or 5- or 6-membered heterocyclic aromatic rings which are substituted by a fluorine atom in at least one of the two ortho-positions to the titanium-carbon bond and contain, as a further substituent, unsubstituted or substituted 1-pyrryl, are suitable as photoinitiators for radiation-induced polymerization of ethylenically unsaturated compounds.

21 Claims, No Drawings

TITANOCENES, THE USE THEREOF, AND N-SUBSTITUTED PYRROLES

The present invention relates to titanocenes containing fluorinated and pyrrole-substituted aromatic radicals, a photopolymerizable composition comprising ethylenically unsaturated compounds which contain these titanocenes as photoinitiators, a substrate coated with this composition, a process for the production of photographic relief images using this coated substrate, and fluoroaromatic-substituted pyrroles.

EP-A-0,122,223 discloses that titanocenes containing fluoroaryl ligands are excellent photoinitiators. The fluoroaryl ligands of these titanocenes may be substituted by heterocycloaliphatic radicals. Substitution by heteroaryl radicals is not mentioned.

The invention relates to titanocenes of the formula I

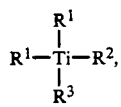
(I)

in which both $R^1$ radicals, independently of one another, are cyclopentadienyl$^-$, indenyl$^-$ or 4,5,6,7-tetrahydroindenyl$^-$, each of which is unsubstituted or mono- or polysubstituted by $C_1$-$C_{18}$alkyl or -alkoxy, $C_2$-$C_{18}$alkenyl, $C_5$-$C_8$cycloalkyl, $C_6$-$C_{16}$aryl, $C_7$-$C_{16}$aralkyl, $SiR_3^4$, $GeR_3^4$, cyano or halogen, or both $R^1$ together are a radical of the formula II

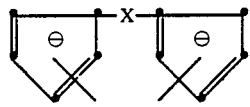
(II)

unsubstituted or substituted as above, in which X is $-(-CH_2-)_n$ where $n = 1$, 2 or 3, unsubstituted or phenyl-substituted alkylidene having 2 to 12 carbon atoms, cycloalkylidene having 5 to 7 ring carbon atoms, $SiR_2^4$, $SiR_2^4$-O-$SiR_2^4$, $GeR_2^4$ or $SnR_2^4$, and $R^4$ is $C_1$-$C_{12}$alkyl, $C_5$-$C_{12}$cycloalkyl, $C_6$-$C_{16}$aryl or $C_7$-$C_{16}$aralkyl, $R^2$ is a 6-membered carbocyclic or 5- or 6-membered heterocyclic aromatic ring which is substituted by fluorine atoms in at least one of the two ortho-positions to the titanium-carbon bond, and in which the aromatic ring may contain further substituents, $R^3$, independently, is as defined for $R^2$ or $R^2$ and $R^3$ together are a radical of the formula III

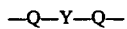 (III)

in which Q is a carbocyclic aromatic ring where the two bonds are each in the ortho-position to the Y group and the second ortho-position to the titanium-carbon bond is in each case substituted by a fluorine atom and where Q may contain further substituents, and Y is $CH_2$, alkylidene having 2 to 12 carbon atoms, cycloalkylidene having 5 to 7 ring carbon atoms, $NR^4$, O, S, SO, $SO_2$, CO, $SiR_2^4$, $GeR_2^4$ or $SnR_2^4$, and $R^4$ is as defined above, wherein, in the titanocenes, $R^2$ and $R^3$ are substituted by a radical of the formula IV

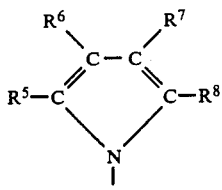
(IV)

in which $R^5$, $R^6$, $R^7$ and $R^8$, independently of one another, are a hydrogen atom, or linear or branched $C_1$-$C_{18}$alkyl, $C_2$-$C_5$alkenyl, $C_7$-$C_9$aralkyl or -alkaryl, $C_8$-$C_{10}$alkaralkyl, $C_6$-$C_{10}$aryl, 2-furyl, $C_5$-$C_8$cycloalkyl, $C_5$-$C_8$cycloalkenyl, $C_2$-$C_{12}$alkanoyl or $C_2$-$C_{12}$alkoxycarbonyl each of which is unsubstituted or substituted by $C_2$-$C_8$dialkylamino or -aminomethyl, bis-[2-($C_1$-$C_4$alkoxy)ethyl]amino or -aminomethyl, morpholino, morpholinylmethyl, piperidino, piperidinylmethyl, N-methylpiperazino, N-methylpiperazinylmethyl, pyrrolidino, pyrrolidinylmethyl, quaternary $C_3$-$C_{10}$trialkylammonium or -ammoniummethyl, $C_1$-$C_{12}$alkoxy, $-OCH_2CH_2)_lO$-$C_1$-$C_{16}$alkyl in which l is a number from 1 to 20, 1,3-dioxolan-2-yl, 4-methyl-1,3-dioxolan-2-yl, $-OCH_2CH_2O-$, $C_2$-$C_{12}$alkoxycarbonyl, $C_2$-$C_{12}$alkanoyloxy, $C_2$-$C_{12}$alkanoyl, $C_1$-$C_{12}$alkylthio, halogen, cyano or $SiR_3^4$ in which $R^4$ is as defined above; or are $-CHO$, $-SiR_3^4$ or $-GeR_3^4$ in which $R^4$ is as defined above; or $R^5$ and $R^6$ and/or $R^7$ and $R^8$ or $R^6$ and $R^7$ in each case together are $-(CH_2)_3-$, $-(CH_2)_4-$, $-CH=CH-CH=CH-$, $-CH=CH-C(R^{11})=CH-$, $-CH_2OCH_2-$ or $-CH_2N(C_1$-$C_4$alkyl)$CH_2-$ in which $R^{11}$ is hydroxyl, $C_1$-$C_4$alkoxy or $C_2$-$C_4$alkanoyloxy.

The $R^1$ groups are preferably identical radicals. Suitable substituents for $R^1$ are: linear or branched alkyl or alkoxy having 1 to 18, particularly 1 to 12 and in particular 1 to 6, carbon atoms, and alkenyl having 2 to 18, particularly 2 to 12, and in particular 2 to 6, carbon atoms, for example methyl, ethyl, propyl, isopropyl, n-butyl, tertbutyl, pentyl, hexyl, octyl, decyl, dodecyl, tetradecyl, hexadecyl, octadecyl and the corresponding alkenyl and alkoxy groups; cycloalkyl having 5 to 8 ring carbon atoms, for example cyclopentyl, cyclohexyl, cycloheptyl, methylcyclopentyl and methylcyclohexyl; aryl having 6 to 16 carbon atoms and aralkyl having 7 to 16 carbon atoms, for example phenyl, naphthyl, benzyl and phenylethyl; cyano and halogen, particularly F, Cl and Br; $SiR_3^4$ or $GeR_3^4$ in which $R^4$ is preferably $C_1$-$C_8$alkyl, cyclohexyl, phenyl or benzyl. Examples of alkyl $R^4$ are methyl, ethyl, n- and i-propyl, n-, i- and t-butyl, pentyl, hexyl, heptyl and octyl.

The $R^1$ radicals may contain up to 5 substituents, but particularly up to 3 substituents. In particular, both $R^1$ are cyclopentadienyl$^-$ or methylcyclopentadienyl$^-$ radicals.

In the formula II, alkylidene X preferably contains 2 to 6 carbon atoms. Examples of alkylidene, which may be unsubstituted or substituted by phenyl, and cycloalkylidene are ethylidene, propylidene, butylidene, hexylidene, phenylmethylene, diphenylmethylene, cyclopentylidene and cyclohexylidene. In the group X, alkyl $R^4$ preferably contains 1 to 6 carbon atoms, and is, for example, methyl, ethyl, propyl, butyl or hexyl, and cycloalkyl $R^4$ is preferably cyclopentyl or cyclohexyl, aryl $R^4$ is preferably phenyl and aralkyl $R^4$ is preferably benzyl. $-CH_2-_nX$ is preferably methylene.

As a 6-membered carbocyclic aromatic and fluorine-substituted ring, $R^2$ may be fluorine-substituted indene, indan, fluorene, naphthaline and particularly phenyl. As a heterocyclic aromatic and 5-membered radical, $R^2$ preferably contains one heteroatom and, as a 6-membered ring, preferably 1 or 2 heteroatoms. Both ortho-positions are preferbly substituted by fluorine. Examples are 4,6-difluoroinden-5-yl, 5,7-difluoroindan-6-yl, 2,4-difluorofluorene-3-yl, 1,3-difluoronaphth-2-yl, 2,6-difluorophen-1-yl, 2,4-difluoropyrr-3-yl, 2,4-difluorofur-3-yl, 2,4-difluorothien-3-yl, 2,4-difluoropyrid-3-yl, 4,6-difluoropyrimidin-5-yl and 3,5-difluoropyridazin-4-yl.

As a radical of the formula III, $R^2$ and $R^3$ may be, for example,

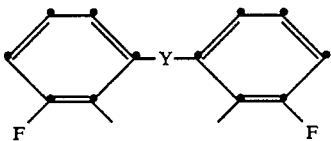

In the formula III and in the formula above, Y is preferably methylene, ethylidene, propylidene, S or O. $R^3$ preferably has the same meaning as $R^2$.

In a preferred embodiment, $R^2$ in the formula I is substituted 2,6-difluorophen-1-yl or $R^2$ and $R^3$ together are a substituted radical of the formula

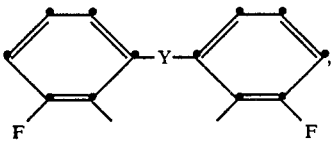

in which Y is as defined above, and are substituted by a radical of the formula IV and may contain further substituents. In particular, $R^2$ is 2,6-difluorophen-1-yl which contains 1 to 3 further substituents, of which at least one is a radical of the formula IV.

In a preferred embodiment, $R^2$ and $R^3$ are 2,6-difluorophen-1-yl to which a radical of the formula IV is bound, and which may contain a further 1 or 2 identical or different substituents.

A preferred group of metallocenes of the formula I are those in which both $R^1$ are cyclopentadienyl$^\ominus$ or $C_1$-$C_4$alkyl-substituted cyclopentadienyl$^\ominus$ and $R^2$ and $R^3$ are radicals of the formula V

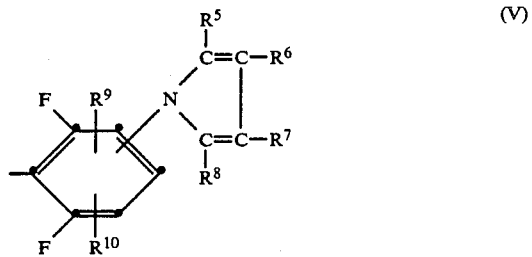 (V)

in which $R^5$, $R^6$, $R^7$ and $R^8$ are as defined above, and $R^9$ and $R^{10}$, independently of one another, are H or F. $R^9$ and $R^{10}$ are preferably H.

In the formula V, the pyrryl group is preferably bound in the ortho-position to an F atom. $R^9$ and $R^{10}$ are preferably H.

Substituents on $R^5$, $R^6$, $R^7$ and $R^8$ are $C_2$-$C_8$-, preferably $C_2$-$C_4$dialkylamino or -aminomethyl, for example dimethyl-, diethyl-, di-n-propyl-, di-n-butyl- or methylethylamino and the corresponding -aminomethyl radicals; bis[2-($C_1$-$C_4$alkoxy)ethyl]amino or -aminomethyl, for example bis(2-methoxyethyl)aminoaminomethyl or bis(2-ethoxyethyl)amino or -aminomethyl; morpholino; morpholinylmethyl; piperidino; piperidinylmethyl; N-methylpiperazino; N-methylpiperazinylmethyl; pyrrolidino; pyrrolidinylmethyl; quaternary $C_3$-$C_{10}$trialkyl-, preferably $C_3$-$C_6$-trialkylammonium or -ammoniummethyl, for example trimethyl-, triethyl, dimethylethyl- or dimethylpropylammonium and the corresponding -ammoniummethyl radicals; $C_1$-$C_{12}$-, preferably $C_1$-$C_4$alkoxy, for example methoxy, ethoxy, propoxy and butoxy;
—$OCH_2CH_2$—$_l$-$OC_1$-$C_{16}$alkyl in which l is preferably a number from 1 to 3, for example $CH_3$—O—$CH_2CH_2O)_2$—; 1,3-dioxolan-2-yl; 4-methyl-1,3-dioxolan-2-yl, —$OCH_2CH_2O$—; $C_2$-$C_{12}$-, preferably $C_2$-$C_6$-alkoxycarbonyl, for example methoxy-, ethoxy-, propoxy- and butoxycarbonyl; $C_2$-$C_{12}$-, preferably $C_2$-$C_6$-alkanoyloxy, for example acetyl-, propionyl- and butyryloxy; $C_2$-$C_{12}$-, preferably $C_2$-$C_6$alkanoyl, for example acetyl, propionyl and butyryl; $C_1$-$C_{12}$-, preferably $C_1$-$C_6$alkylthio, for example methyl-, ethyl-, propyl- and butylthio; halogen, preferably F, Cl and Br; cyano; $SiR_3^4$ in which $R^4$ is preferably $C_1$-$C_6$alkyl, for example butyl, propyl, ethyl and particularly methyl.

Of the substituents, those from the group comprising $C_2$-$C_8$dialkylamino or -aminomethyl, bis(2-methoxyethyl)amino or -aminomethyl, morpholino, morpholinylmethyl, N-methylpiperidino, N-methylpiperidinylmethyl, $C_1$-$C_{12}$alkyldimethylammonium or -ammonium methyl, $C_1$-$C_{12}$-alkoxy, —($-OCH_2CH_2$—)—$_l$—O—$C_1$-$C_{12}$alkyl where $l$=1 to 3, 1,3-dioxolan-2-yl, —$CH_2CH_2O$—, $C_2$-$C_8$alkanoyloxy, $C_2$-$C_8$alkanoyl, $C_1$-$C_8$alkoxycarbonyl, halogen, cyano, formyl, $C_1$-$C_4$-alkylthio and trimethylsilyl are preferred. A particularly preferred group of substituents are selected from $C_2$-$C_8$dialkylamino or -aminomethyl, bis(2-methoxyethyl)amino or -aminomethyl, morpholino, morpholinylmethyl, $C_1$-$C_4$-alkoxy, 1,3-dioxolan-2-yl and cyano. The $R^5$, $R^6$, $R^7$ and $R^8$ radicals may be monosubstituted or polysubstituted, preferably monosubstituted to trisubstituted and particularly monosubstituted. In a preferred embodiment, only the alkyl $R^5$, $R^6$, $R^7$ and $R^8$ radicals are substituted as defined.

Alkyl $R^5$, $R^6$, $R^7$ and $R^8$ preferably contain 1 to 12 and particularly 1 to 8 carbon atoms. Examples are methyl, ethyl and the isomers of propyl, butyl, pentyl, hexyl, heptyl, octyl, nonyl, decyl, undecyl, dodecyl, tridecyl, tetradecyl, hexadecyl and octadecyl. Alkenyl $R^5$, $R^6$, $R^7$ and $R^8$ preferably contain 2 to 4 carbon atoms. Examples are vinyl, allyl, crotonyl, 2-methyl-prop-1-en-1-yl, but-1-en-1-yl, but-2-en-2-yl, but-2-en-1-yl, but-3-en-1-yl or -2-yl, or pent-1-en-1-yl. Aryl $R^5$, $R^6$, $R^7$ and $R^8$ are, in particular, phenyl. Aralkyl or alkaryl $R^5$, $R^6$, $R^7$ and $R^8$ may be, for example, benzyl, phenylethyl, phenylpropyl, methylphenyl, ethylphenyl, propylphenyl, dimethylphenyl and methylethylphenyl. Alkaralkyl $R^5$, $R^6$, $R^7$ and $R^8$ may be, for example, methylbenzyl, ethylbenzyl, propylbenzyl, (methylphenyl)ethyl or dimethylbenzyl. Cycloalkyl and cycloalkenyl $R^5$, $R^6$, $R^7$ and $R^8$ are, in particular, cyclopentyl, cyclopentenyl, cyclohexyl or cyclohexenyl. Alkanoyl $R^5$, $R^6$, $R^7$ and $R^8$ preferably contain 2 to 8, particularly 2 to 6, carbon atoms. Examples are acetyl, propionyl, butanoyl, pentanoyl, hexanoyl, octanoyl and dodecanoyl. $C_2-C_{12}$-alkoxycarbonyl $R^5$, $R^6$, $R^7$ and $R^8$ are, in particular, $C_2-C_5$-alkoxycarbonyl, for example methoxycarbonyl, ethoxycarbonyl or butoxycarbonyl. $R^5$, $R^6$, $R^7$ and $R^8$ may be the $-GeR_3^4$ groups and preferably $-SiR_3^4$. In these groups, $R^4$ is preferably $C_1-C_{12}$-, preferably $C_1-C_8$- and in particular $C_1-C_4$alkyl. The $-Si(CH_3)_3$ group is particularly preferred.

In a preferred sub-group, $R^5$, $R^6$, $R^7$ and $R^8$, independently of one another, are a hydrogen atom or unsubstituted or substituted $C_1-C_{12}$-alkyl, $C_2-C_5$alkenyl, $C_7$- or $C_8$aralkyl or -alkaryl, phenyl, 2-furyl, $C_5$- or $C_6$cycloalkyl, $C_5$- or $C_6$cycloalkenyl, $C_2-C_8$alkanoyl, $C_2-C_5$alkoxycarbonyl, —CHO or $SiR_3$ in which $R^4$ is $C_1-C_8$alkyl.

In another preferred sub-group, $R^5$, $R^6$, $R^7$ and $R^8$, independently of one another, are a hydrogen atom, or unsubstituted or substituted $C_1-C_8$alkyl, $C_2-C_4$alkenyl, benzyl, phenyl, 2-furyl, $C_5$- or $C_6$cycloalkyl, $C_2-C_6$alkanoyl, $C_2-C_5$alkoxycarbonyl, —CHO or $SiR_3^4$ in which $R^4$ is $C_1-C_4$alkyl.

In a further preferred sub-group, $R^5$, $R^6$, $R^7$ and $R^8$, independently of one another, are a hydrogen atom or unsubstituted or substituted $C_1-C_8$alkyl, $C_2-C_4$alkenyl, phenyl, 2-furyl or $SiR_3^4$ in which $R^4$ is $C_1-C_4$alkyl.

In a preferred embodiment, $R^6$ or $R^6$ and $R^7$ in the formula IV are a hydrogen atom.

Some examples of compounds of the formula I are:
Bis(cyclopentadienyl)bis[2,6-difluoro-3-(2,5-dimethylpyrr-1-yl)phenyl]titanium
Bis(trimethylsilylcyclopentadienyl)bis[2,6-difluoro-3-(2,5-dimethylpyrr-1-yl)phenyl]titanium
Bis(methylcyclopentadienyl)bis[2,6-difluoro-3-(2,5-dimethylpyrr-1-yl)phenyl]titanium
Bis(cyclopentadienyl)bis[2,6-difluoro-3-(2-isopropyl-5-methylpyrr-1-yl)phenyl]titanium
Bis(cyclopentadienyl)bis[2,6-difluoro-3-(2-(1-ethylpentyl)-5-methylpyrr-1-yl)phenyl]titanium
Bis(cyclopentadienyl)bis[2,6-difluoro-3-(2-(2-methoxyethyl)-5-methylpyrr-1-yl)phenyl]titanium
Bis(cyclopentadienyl)bis[2,6-difluoro-3-(5-methyl-2-phenylpyrr-1-yl)phenyl]titanium
Bis(cyclopentadienyl)bis[2,6-difluoro-3-(2-(2-furyl)-5-methylpyrr-1-yl)phenyl]titanium
Bis(cyclopentadienyl)bis[2,6-difluoro-3-(2,5-bis(2-methylprop-1-enyl)pyrr-1-yl)phenyl]titanium
Bis(cyclopentadienyl)bis[2,6-difluoro-3-(2,5-dimethyl-3-(2-methylprop-1-enyl)pyrr-1-yl)phenyl]titanium
Bis(cyclopentadienyl)bis[2,6-difluoro-3-(2,5-dimethyl-3-(trimethylsilyl)pyrr-1-yl)phenyl]titanium
Bis(cyclopentadienyl)bis[2,6-difluoro-3-(pyrr-1-yl)phenyl]titanium
Bis(cyclopentadienyl)bis[2,6-difluoro-3-(2,5-bis(dimethylaminomethyl)pyrr-1-yl)phenyl]titanium
Bis(cyclopentadienyl)bis[2,6-difluoro-3-(2,5-bis(bis(2-methoxyethyl)aminomethyl)pyrr-1-yl)phenyl]titanium
Bis(cyclopentadienyl)bis[2,6-difluoro-3-(2,5-dimethyl-3-(dimethylaminomethyl)-pyrr-1-yl)phenyl]titanium
Bis(cyclopentadienyl)bis[2,6-difluoro-3-(2,5-dimethyl-3,4-bis(dimethylaminomethyl)-pyrr-1-yl)phenyl]titanium
Bis(cyclopentadienyl)bis[2,6-difluoro-3-(2,5-dimethyl-3-(trimethylammoniummethyl)-pyrr-1-yl)phenyl]titanium chloride
Bis(cyclopentadienyl)bis[2,6-difluoro-3-(2,5-dimethyl-3-(bis(2-methoxyethyl)amino)methyl)pyrr-1-yl)phenyl]titanium
Bis(cyclopentadienyl)bis[2,6-difluoro-3-(2,5-dimethyl-3-(morpholino)methyl)pyrr-1-yl)phenyl]titanium
Bis(methylcyclopentadienyl)bis[2,6-difluoro-3-(2,5-dimethyl-3-((dibutylamino)methyl)pyrr-1-yl)phenyl]titanium
Bis(cyclopentadienyl)bis[2,6-difluoro-3-(2,5-dimethyl-3-((ethyloxy)methyl)pyrr-1-yl)phenyl]titanium
Bis(cyclopentadienyl)bis[2,3,5,6-tetrafluoro-4-(2,5-dimethyl-3-((4-methyl-1-piperazinyl)methyl)pyrr-1-yl)phenyl]titanium
Bis(cyclopentadienyl)bis[2,3,5,6-tetrafluoro-4-(2-(1-ethylpentyl)-5-methylpyrr-1-yl)phenyl]titanium
Bis(cyclopentadienyl)bis[2,6-difluoro-3-(2,5-dimethyl-3-((dimethoxy)methyl)pyrr-1-yl)phenyl]titanium
Bis(methylcyclopentadienyl)bis[2,6-difluoro-3-(5-isopropyl-2-methyl-3-((diethoxy)methyl)pyrr-1-yl)phenyl]titanium
Bis(cyclopentadienyl)bis[2,6-difluoro-3-(2,5-dimethyl-3-(1,3-dioxolan-2-yl)pyrr-1-yl)phenyl]titanium
Bis(cyclopentadienyl)bis[2,6-difluoro-3-(2-(4-methyl-1,3-dioxolan-2-yl)pyrr-1-yl)phenyl]titanium
Bis(cyclopentadienyl)bis[2,6-difluoro-3-(1,1-ethylenedioxy-ethyl)pyrr-1-yl)phenyl]titanium
Bis(cyclopentadienyl)bis[2,6-difluoro-3-(2,5-bis(2,2-diethoxyethyl)pyrr-1-yl)phenyl]titanium
Bis(cyclopentadienyl)bis[2,6-difluoro-3-(2-methyl-3-(dimethoxy-methyl)-5-(2,2-dimethoxy-ethyl)pyrr-1-yl)phenyl]titanium
Bis(cyclopentadienyl)bis[2,6-difluoro-3-(2,5-dimethyl-3-(diethoxymethyl)pyrr-1-yl)phenyl]titanium
Bis(cyclopentadienyl)bis[2,6-difluoro-3-(5-methyl-2-(2,2-dimethoxyethyl)pyrr-1-yl)phenyl]titanium
Bis(methylcyclopentadienyl)bis[2,6-difluoro-3-(2,5-dimethyl-3-propylthiopyrr-1-yl)phenyl]titanium
Bis(trimethylsilylcyclopentadienyl)bis[2,6-difluoro-3-(2,5-dimethyl-3-trimethylsilypyrr-1-yl)phenyl]titanium
Bis(cyclopentadienyl)bis[2,6-difluoro-3-(2,5-diethoxymethyl-pyrr-1-yl)phenyl]titanium
Bis(cyclopentadienyl)bis[2,6-difluoro-3-(2-methyl-4,6-dihydro-1H-furo[3,4-b]pyrr-1-yl)phenyl]titanium
Bis(cyclopentadienyl)bis[2,6-difluoro-3-(4,6-dimethyl-3,5-dihydro-1H-furo[3,4-c]pyrr-5-yl)phenyl]titanium
Bis(cyclopentadienyl)bis[2,6-difluoro-3-(2,5-dimethyl-1,4,5,6-tetrahydropyrrolo[3,4-b]pyrr-1-yl)phenyl]titanium
Bis(cyclopentadienyl)bis[2,6-difluoro-3-(1,3,5-trimethyl-2,4,5,6-tetrahydropyrrolo[3,4-c]pyrr-2-yl)phenyl]titanium
Bis(cyclopentadienyl)bis[2,6-difluoro-3-(1,4,5,7-tetrahydro-3H-difuro[3,4-b:3',4'-d]pyrr-4-yl)phenyl]titanium
Bis(cyclopentadienyl)bis[2,6-difluoro-3-(2,6-dimethyl-2,3,4,5,6,7-hexahydro-1H-dipyrrolo[3,4-b:3'-4'-d]pyrr-4-yl)phenyl]titanium
Bis(cyclopentadienyl)bis[2,6-difluoro-3-(6-methyl-1,3,4,5,6,7-hexahydrofuro[3,4-b]pyrrolo[3,4-d]pyrr-4-yl)phenyl]titanium
Bis(cyclopentadienyl)bis[2,6-difluoro-3-(2-isobutyl-5-methyl-pyrr-1-yl)phenyl]titanium
Bis(cyclopentadienyl)bis[2,6-difluoro-3-(2-(1-ethylpentyl)-5-methylpyrr-1-yl)phenyl]titanium
Bis(cyclopentadienyl)bis[2,6-difluoro-3-(2-(cyclohex-3-enyl)-5-methyl-pyrr-1-yl)phenyl]titanium
Bis(cyclopentadienyl)bis[2,6-difluoro-3-(2-(6-methyl-6-methoxyheptyl)-5-methylpyrr-1-yl)phenyl]titanium Bis(cyclopentadienyl)bis[2,6-difluoro-3-(2-(1,1-dimethyl-2-methoxyethyl)-5-methypyrr-1-yl)phenyl]titanium
Bis(cyclopentadienyl)bis[2,6-difluoro-3-methyl-4-(2,5-dimethyl-3-(2-methylprop-1-enyl)pyrr-1-yl)phenyl]titanium
Bis(cyclopentadienyl)bis[2,6-difluoro-5-methyl-3-(2,5-dimethyl-3-(ethoxymethyl)pyrr-1-yl)phenyl]titanium
Bis(cyclopentadienyl)bis[2,6-difluoro-5-chloro-3-(5-methyl-2-(1-ethylpentyl)pyrr-1-yl)phenyl]titanium
Bis(cyclopentadienyl)bis[2,4,6-trifluoro-3-(pyrr-1-yl)phenyl]titanium
Bis(cyclopentadienyl)bis[2,5,6-trifluoro-3-(2,5-dimethylpyrr-1-yl)phenyl]titanium
Bis(cyclopentadienyl)bis[4-bromo-2,6-difluoro-3-(pyrr-1-yl)phenyl]titanium
Bis(cyclopentadienyl)bis[2,4,5,6-tetrafluoro-3-(2,5-dimethylpyrr-1-yl)phenyl]titanium
Bis(cyclopentadienyl)bis[2,4,5,6-tetrafluoro-3-(pyrr-1-yl)phenyl]titanium
Bis(cyclopentadienyl)bis[4-methyl-2,5,6-trifluoro-3-(pyrr-1-yl)phenyl]titanium
Bis(cyclopentadienyl)bis[2,6-difluoro-3-(2,5-diethylpyrr-1-yl)phenyl]titanium
Bis(cyclopentadienyl)bis[2,6-difluoro-3-(2,5-dimethyl-3-ethoxycarbonylpyrr-1-yl)phenyl]titanium
Bis(cyclopentadienyl)bis[2,6-difluoro-3-(2,3,4,5-tetramethylpyrr-1-yl)phenyl]titanium
Bis(cyclopentadienyl)bis[2,6-difluoro-3-(2,3,5-trimethylpyrr-1-yl)phenyl]titanium
Bis(cyclopentadienyl)bis[2,6-difluoro-3-(2,4-dimethylpyrr-1-yl)phenyl]titanium
Bis(cyclopentadienyl)bis[2,6-difluoro-3-(3,4-dimethylpyrr-1-yl)phenyl]titanium
Bis(cyclopentadienyl)bis[2,6-difluoro-3-(2-(2,5-dioxahexyl)-5-methylpyrr-1-yl)phenyl]titanium
Bis(cyclopentadienyl)bis[2,6-difluoro-3-(2-(2,5-dioxanonyl)-5-methylpyrr-1-yl)phenyl]titanium
Bis(cyclopentadienyl)bis[2,6-difluoro-3-(4,5,6,7-tetrahydro-2H-isoindol-2-yl)phenyl]titanium
Bis(cyclopentadienyl)bis[2,6-difluoro-3-(2H-isoindol-2-yl)phenyl]titanium
Bis(cyclopentadienyl)bis[2,6-difluoro-3-(1,3-diphenyl-1H-isoindol-2-yl)phenyl]titanium
Bis(cyclopentadienyl)bis[2,6-difluoro-3-(1,4,5,6-tetrahydrocyclopenta[b]pyrr-1-yl)phenyl]titanium
Bis(cyclopentadienyl)bis[2,6-difluoro-3-(1,4,5,6-tetrahydro-2-phenylcyclopenta[b]pyrr-1-yl)phenyl]titanium
Bis(cyclopentadienyl)bis[2,6-difluoro-3-(1,4,5,6-tetrahydro-2-methylcyclopenta[b]pyrr-1-yl)phenyl]titanium
Bis(cyclopentadienyl)bis[2,6-difluoro-3-(4,5,6,7-tetrahydro-1H-indol-1-yl)phenyl]titanium
Bis(cyclopentadienyl)bis[2,6-difluoro-3-(4,5,6,7-tetrahydro-2-phenyl-1H-indol-1-yl)phenyl]titanium
Bis(cyclopentadienyl)bis[2,6-difluoro-3-(4,5,6,7-tetrahydro-2-methyl-1H-indol-1-yl)phenyl]titanium
Bis(cyclopentadienyl)bis[2,6-difluoro-3-(2,3,4,5,6,7-hexahydro-1H-dicyclopenta[b,d]pyrr-1-yl)phenyl]titanium
Bis(cyclopentadienyl)bis[2,6-difluoro-3-(2,3,4,5,6,7,8,9-octahydro-1H-carbazol-9-yl)phenyl]titanium
Bis(cyclopentadienyl)bis[2,6-difluoro-3-(2,3,4,9-tetrahydro-1H-carbazol-9-yl)phenyl]titanium
Bis(cyclopentadienyl)bis[2,6-difluoro-3-(2,3,4,9-tetrahydro-6-methoxy-1H-carbazol-9-yl)phenyl]titanium
Bis(cyclopentadienyl)bis[2,6-difluoro-3-(9H-carbazol-9-yl)phenyl]titanium
Bis(cyclopentadienyl)bis[2,6-difluoro-4-(9H-carbazol-9-yl)phenyl]titanium
Bis(cyclopentadienyl)bis[2,3,5,6-tetrafluoro-4-(9H-carbazol-9-yl)phenyl]titanium
Bis(cyclopentadienyl)bis[2,4,6-trifluoro-5-methyl-3-(9H-carbazol-9-yl)phenyl]titanium
Bis(cyclopentadienyl)bis[2,5,6-trifluoro-3-(9H-carbazol-9-yl)phenyl]titanium
Bis(cyclopentadienyl)bis[2,6-difluoro-3-(1H-indol-1-yl)phenyl]titanium
Bis(cyclopentadienyl)bis[2,6-difluoro-3-(2-methyl-1H-indol-1-yl)phenyl]titanium
Bis(cyclopentadienyl)bis[2,6-difluoro-3-(2-methoxycarbonyl-1H-indol-1-yl)phenyl]titanium
Bis(cyclopentadienyl)bis[2,6-difluoro-3-(2-ethoxycarbonyl-1H-indol-1-yl)phenyl]titanium
Bis(cyclopentadienyl)bis[2,6-difluoro-3-(5-hydroxy-2-methyl-1H-indol-1-yl)phenyl]titanium
Bis(cyclopentadienyl)bis[2,6-difluoro-3-(5-methoxy-2-methyl-1H-indol-1-yl)phenyl]titanium
Bis(cyclopentadienyl)bis[2,6-difluoro-3-(5-acetoxy-2-methyl-1H-indol-1-yl)phenyl]titanium
Bis(cyclopentadienyl)bis[2,6-difluoro-3-(5-hydroxy-3-methyl-1H-indol-1-yl)phenyl]titanium
Bis(cyclopentadienyl)bis[2,6-difluoro-3-(2,3-dimethyl-1H-indol-1-yl)phenyl]titanium
Bis(cyclopentadienyl)bis[2,3,5,6-tetrafluoro-4-(2,3-dimethyl-1H-indol-1-yl)phenyl]titanium The titanocenes of the formula I can be prepared by known or analogous processes by reacting 1 mole of a compound of the formula VI

in which $R^1$ is as defined above and Z is halogen, particularly chlorine, with one mole of $LiR^2$ and with one mole of $LiR^3$ or with 1 mole of $Li_2QYQ$, where $R^2$, $R^3$ and QYQ are as defined above, and then isolating the compounds of the formula I in a manner known per se.

The known processes are described, for example, in J. Organometal. Chem., 2 (1964) 206–212, J. Organometal. Chem., 4 (1965) 445–446 and in EP-A-0,122,223.

The starting compounds of the formula VI, in which Z is, in particular, chlorine, are known or can be obtained by analogous processes by reacting $TiCl_4$ with sodium compounds $NaR^1$. The lithium compounds $LiR^2$ and $Li_2QYQ$ are new. They can be prepared by processes known per se by reacting, for example, butyllithium with compounds of the formula VII.

The invention further relates to compounds of the formula VII

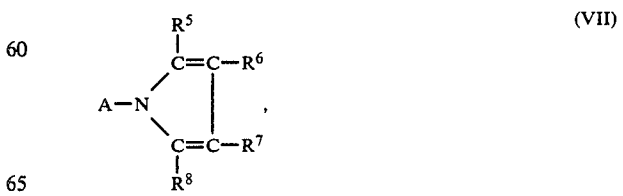

in which A is a 6-membered carbocyclic or 5- or 6-membered heterocyclic aromatic ring which contains at least one fluorine atom, a hydrogen atom or a halogen atom in the ortho-position thereto, and, if appropriate, further substituents, or A is a radical of the formula

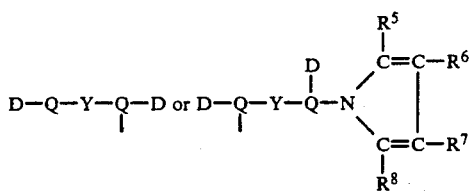

in which D is a hydrogen atom or halogen atom bound in the ortho-position to Y, Q is a carbocyclic aromatic ring which is substituted in each case by a fluorine atom in the ortho-position to the D group, and Q may contain further substituents, and Y, $R^5$, $R^6$, $R^7$ and $R^8$ are as defined above, with the exception of 3,4-dimethyl-1-(pentafluoro-phenyl)pyrrole.

The same embodiments and preferences as described above for $R^2$ or $R^2$ and $R^3$ together and for the radical of the formula IV apply correspondingly to A, $R^5$, $R^6$, $R^7$, $R^8$, Q and Y.

As a 6-membered carbocyclic or 5- or 6-membered heterocyclic aromatic ring, the radical A preferably contains a further fluorine atom in the ortho-position to the hydrogen or halogen atom. The halogen atom is preferably selected from F, Cl or Br. The aromatic ring is preferably a phenyl ring. A hydrogen atom, in particular, is bound in the ortho-position to the fluorine atom or to Y. The pyrrole group is preferably bound in the ortho-position to an F atom. It has been found that the H atom adjacent to the F atom in such compounds can surprisingly be replaced directly by lithium. A preferred group of compounds is those of the formula VIIa

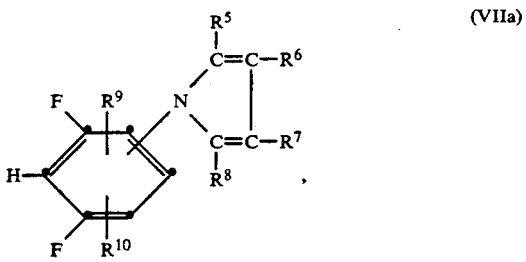

(VIIa)

in which $R^9$ and $R^{10}$, independently of one another, are H or F, particularly H, and $R^5$, $R^6$, $R^7$ and $R^8$ are as defined above. The pyrrole group is preferably bound in the ortho-position to the fluorine atom.

The compounds of the formula VII can be prepared by processes known per se. 3,4-dimethyl-1-(pentafluorophenyl)pyrrol is described by U. Jager et al. in Chem. Ber. 119, pp. 3405-3410 (1986). A general preparation possibility is the reaction of amines of the formula A-NH₂ with substituted or unsubstituted 1,4-diketones, 1,4-dialdehydes or 1,4-ketoaldehydes (Paal-Knorr synthesis). This reaction is described, for example, in Comprehensive Organic Chemistry, Vol. 4, 299 and in J. Chem. Soc., 1952, 1467. The amines and diketones and dialdehydes are known, in some cases commercially available or preparable by known processes.

Compounds of the formula VII in which $R^5$ and $R^8$ are H are also obtained by reacting amines A-NH₂ with substituted or unsubstituted 2,5-dimethoxytetrahydrofuran or 2,5-diacetoxytetrahydrofuran, cf. G. Stefancich et al, Farmaco Ed. Sc. 40, 237–248 (1985) and Houben-Weyl, Volume 6/3, 730.

Further syntheses of compounds of the formula VII from the amines A-NH₂ are the reaction with 2,2'-(ethane-1,2-diyl)bis-1,3-dioxolanes, the reaction with 2-alkyne-1,4-diols or the reaction with α-haloketones and β-ketoesters (Hantzsch synthesis), cf. Comprehensive Organic Chemistry, Vol. 4, 298.

Compounds of the formula VII having an indole structure can be prepared, for example, by the Neuitzescu synthesis or by the Bischler synthesis (Comprehensive Organic Chemistry, Vol. 4, 461 and 462). Compounds of the formula VII having an isoindole structure can be prepared, for example, from the corresponding phthalimides by reduction using complex metal hydrides (Houben-Weyl, Volume 4/Id, 258). Compounds of the formula VII having a carbazole structure can be prepared, for example, by the method of Dunlop and Tucker (J. Chem. Soc. 1939, 1945).

It is possible to subsequently introduce substituents into unsubstituted or partly substituted pyrrole derivatives of the formula VII. Silyl groups can be introduced using silyl trifluoromethanesulfonates [G. Simchen, Tetrahedron 42(5), p. 1299 (1986)]. Furthermore, formylation can be effected by means of POCl₃/DMF [G. F. Smith, J. Chem. Soc., 1954. 3842]. Acylation can be effected by means of ROCl or (RCO)₂O and AlCl₃, cf. J. Rockach et al., Tetrahedron Letters, 22, 4901 (1981) and M. Kakushima et al., J. Org. Chem., 48, 3214 (1983). The formyl group or acyl group can be further derivatized in the context of the invention; for example a $C_2$–$C_5$alkenyl group can be formed by means of a Wittig reaction.

The metallocenes of the formula I are generally prepared in the presence of inert solvents, for example hydrocarbons or ethers, at temperature of from −30° to −100° C., preferably −60° to −90° C., and under a protective-gas atmosphere. In one embodiment of the process, $LiR^2$ or $LiR^3$ is initially prepared by reacting the appropriate halides with butyllithium in an ether as solvent, for example tetrahydrofuran, at temperatures of around −78° C. The appropriate titanocene dihalide is then added to the cooled reaction mixture, the cooling is removed, and the mixture is allowed to warm to room temperature. The reaction mixture is then filtered, if appropriate after adding solvents, and the titanocene according to the invention is isolated from the solution by precipitation or evaporation of the solution.

The compounds are generally crystalline and usually orange-coloured and are distinguished by high thermal stability and only decompose at high temperatures. No decomposition is observed under the action of air or under the action of water. The compounds can be dissolved in curable compositions, even in relatively large amounts, and therefore offer valuable applicational properties. The compounds are also readily soluble in solvents, and can be incorporated in the form of solutions into curable compositions, after which the solvent is removed, if desired.

The compounds have a long shelf life in the dark and can be handled without a protective gas. They are highly suitable on their own as very effective photoinitiators for photoinduced polymerization of ethylenically unsaturated compounds. In this application, they are distinguished by very high photosensitivity and activity over a broad wavelength range from about 200 nm (UV light) to about 600 nm. The titanocenes are furthermore also capable of effectively initiating polymerization under the influence of heat, in which case warming to 170° C. to 240° C. is expedient. It is of course also possible to use the action of light and warming for polymerization, in which case warming after exposure allows lower temperatures, for example 80°-150° C., for the polymerization. Surprisingly, the photosensitivity is higher than in the case of pyrrolidine derivatives.

The present invention furthermore relates to a radiation-polymerizable composition containing (a) at least one non-volatile, monomeric, oligomeric or polymeric compound containing at least one polymerizable, ethylenically unsaturated double bond and (b) at least one titanocene of the formula I as photoinitiator.

The compositions may contain further photoinitiators (c) other than (b), for example those of the benzoin alkyl ether, benzophenone, benzil ketal, 4-aroyl-1,3-dioxolane, dialkoxyacetophenone, α-hydroxy- or α-aminoacetophenone or α-hydroxycycloalkyl phenyl ketone type, or mixtures thereof. The advantage is that it is possible to use smaller amounts of the titanocenes according to the invention and nevertheless achieve the same or improved photosensitivities. The weight ratio (c):(b) of these components may be, for example, from 1:1 to 30:1, preferably 5:1 to 15:1.

The added amounts of titanocenes according to the invention depends essentially on economic points of view, their solubilities and on the sensitivity desired. In general, 0.01 to 20, preferably 0.05-10 and particularly 0.1 to 5, % by weight are used, based on component (a).

As component (a), ethylenically unsaturated, monomeric, oligomeric and polymeric compounds which react by photopolymerization to form high-molecular-weight compounds while modifying their solubility are suitable.

Particularly suitable are, for example, esters of ethylenically unsaturated carboxylic acids and polyols or polyepoxides, and polymers containing ethylenically unsaturated groups in the chain or in the side groups, for example unsaturated polyesters, polyamides and polyurethanes and copolymers thereof, polybutadiene and butadiene copolymers, polyisoprene and isoprene copolymers, polymers and copolymers containing (meth)acrylic groups in the side chain, and mixtures of one or more such polymers.

Examples of unsaturated carboxylic acids are acrylic acid, methacrylic acid, crotonic acid, itaconic acid, cinnamic acid and unsaturated fatty acids, such as linolenic acid or oleic acid. Acrylic acid and methacrylic acid are preferred.

Suitable polyols are aromatic and, particularly, aliphatic and cycloaliphatic polyols. Examples of aromatic polyols are hydroquinone, 4,4'-dihydroxydiphenyl, 2,2-di(4-hydroxyphenyl)propane, and novolaks and resols. Examples of polyepoxides are those based on the polyols mentioned, particularly on the aromatic polyols and epichlorohydrin. Suitable polyols are furthermore also polymers or copolymers which contain hydroxyl groups in the polymer chain or in side groups, for example polyvinyl alcohol and copolymers thereof or hydroxyalkyl polymethacrylates or copolymers thereof. Further suitable polyols are oligoesters containing hydroxyl end groups.

Examples of aliphatic and cycloaliphatic polyols are alkylenediols, preferably having 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols, preferably having molecular weights of from 200 to 1500, 1,3-cyclopentanediol, 1,2-, 1,3- or 1,4-cyclohexanediol, 1,4-dihydroxymethyl-cyclohexane glycerol, tris(β-hydroxyethyl)amine, trimethylolethane, trimethylolpropane, pentaerythritol, dipentaerythritol and sorbitol.

The polyols may be partially or completely esterified with one or various unsaturated carboxylic acids, it being possible for the free hydroxyl groups in partial esters to be modified, for example etherified or esterified with other carboxylic acids.

Examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol, octamethacrylate, pentaerythritol diitaconate, dipentaerythritol trisitaconate, dipentaerythritol pentaitaconate, dipentaerythritol hexaitaconate, ethylene glycol dimethacrylate, 1,3-butanediol diacrylate, 1,3-butanediol dimethacrylate, 1,4-butanediol diitaconate, sorbitol triacrylate, sorbitol tetraacrylate, pentaerythritol modified triacrylate, sorbitol tetramethacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol having molecular weights of from 200-1500, or mixtures thereof.

The amides of identical or different unsaturated carboxylic acids of aromatic, cycloaliphatic and aliphatic polyamines, preferably having 2 to 6, particularly 2 to 4, amino groups are also suitable as component (a). Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetraamine, di-(β-aminoethoxy)- or di(β-aminopropoxy)ethane. Further suitable polyamines are polymers and copolymers containing amino groups in the side chain and oligoamides containing amino end groups.

Examples of unsaturated amides of this type are: methylene bisacrylamide, 1,6-hexamethylene bis-acrylamide, diethylenetriamine tris-methacrylamide, bis(methacrylamidopropoxy)ethane, β-methacrylamidoethyl methacrylate and N-[(β-hydroxyethoxy)ethyl]acrylamide.

Suitable unsaturated polyesters and polyamides are derived, for example, from maleic acid and diols or diamines. Maleic acid may be replaced in part by other dicarboxylic acids. They may be employed together with ethylenically unsaturated comonomers, for example styrene. The polyesters and polyamides may also be derived from dicarboxylic acids and ethylenically unsaturated diols or diamines, particularly from relatively long-chain ones having, for example, 6 to 20 carbon atoms. Examples of polyurethanes are those built up from saturated or unsaturated diisocyanates and unsaturated or saturated diols.

Polybutadiene and polyisoprene and copolymers thereof are known. Suitable comonomers are, for example, olefins such as ethylene, propene, butene, hexene, (meth)acrylates, acrylonitrile, styrene or vinyl chloride. Polymers containing (meth)acrylate groups in the side chain are likewise known. They may be, for example, products of the reaction of epoxy resins based on novolak with (meth)acrylic acid, homopolymers or copolymers of polyvinyl alcohol or hydroxyalkyl derivatives thereof which have been esterified with (meth)acrylic acid, or homopolymers and copolymers of (meth)acrylates which have been esterified with hydroxyalkyl (meth)acrylates.

The photopolymerizable compounds may be employed alone or in any desired mixtures. Mixtures of polyol (meth)acrylates are preferably used.

It is also possible to add binders to the compositions according to the invention, which is particularly expedient if the photopolymerizable compounds are liquid or viscous substances. The amount of binder may be, for example, 5-95, preferably 10-90 and particularly 50-90% by weight, based on the total composition. The choice of binder depends on the area of application and on the properties required for this, such as developability in aqueous and organic solvent systems, adhesion to substrates and oxygen sensitivity.

Suitable binders are, for example, polymers having a molecular weight of from about 5000-2,000,000, preferably 10,000 to 1,000,000. Examples are: homopolymeric and copolymeric acrylates and methacrylates, for example copolymers made from methyl methacrylate/ethyl acrylate/methacrylic acid, polyalkyl methacrylates and polyalkyl acrylates; cellulose esters and ethers, such as cellulose acetate, cellulose acetate butyrate, methylcellulose and ethylcellulose; polyvinyl butyral, polyvinyl formal, cyclized rubber, polyethers, such as polyethylene oxide, polypropylene oxide and polytetrahydrofuran; polystyrene, polycarbonate, polyurethane, chlorinated polyolefins, polyvinyl chloride, copolymers made from vinyl chloride/vinylidene chloride, copolymers of vinylidene chloride with acrylonitrile, methyl methacrylate and vinyl acetate, polyvinyl acetate, copoly(ethylene/vinyl acetate), polyamides, such as polycaprolactam and poly(hexamethylene adipamide), and polyesters, such as poly(ethylene glycol terephthalate) and poly(hexamethylene glycol succinate).

The compositions according to the invention are suitable as coating agents for substrates of all types, for example wood, paper, ceramics, plastics, such as polyester and cellulose acetate films, and metals, such as copper and aluminum, on which a protective coating or photographic image is to be applied by photopolymerization. The present invention furthermore relates to the coated substrates and to a process for applying photographic images onto the substrates. The coated substrates can also be used as recording materials for holograms (volume/phase diagram), in which case it is advantageous that wet development is not necessary for this purpose.

The substrates can be coated by applying a liquid composition, a solution or suspension to the substrate. Liquid compositions without solvent are preferred. In this case, it may be expedient to employ the titanocenes according to the invention in the form of a liquid photoinitiator mixture containing other photoinitiators, for example a benzil ketal, a 4-aroyl-1,3-dioxolane, a dialkoxyacetophenone, an α-hydroxy-or α-aminoacetophenone, an α-hydroxycycloalkyl phenyl ketone or mixtures thereof. Liquid mixtures of liquid to solid photoinitiators and liquid titanocenes or liquid photoinitiators and syrupy to solid titanocenes are particularly advantageous. These mixtures offer applicational advantages and are distinguished by long shelf lives in the dark.

Examples of benzil ketals are those of the formula $$\text{Ph-C(=O)-C(OR}^{13}\text{)(OR}^{14}\text{)-Ph}$$

$R^{13} = R^{14} = $ —$CH_3$
—$CH_2CH_3$
—$(CH_2)_2CH_3$
—$(CH_2)_3CH_3$
—$CH_2CH_2CH(CH_3)_2$

—$CH_2$—$CH$—$C_4H_9$
       |
       $C_2H_5$

—$(CH_2)_9CH_3$
—$C_{10}H_{21}$-iso
—$C_{12}H_{25}$-n
—$C_9H_{19}$ bis-$C_{11}H_{23}$— mixture
—$C_{12}$—$H_{25}$-bis-$C_{15}H_{31}$— mixture
—$CH_2CH$=$CH_2$
—$CH(CH_3)CH$=$CH_2$
—$CH_2CH_2OC_3H_7$-iso
—$CH_2CH_2OC_4H_9$
—$CH_2CH_2OCH_2CH$=$CH_2$
—$CH(CH_3)$—$CH_2OC_4H_9$
—$CH_2COOCH_3$
—$CH_2COOC_4H_9$
—$CH(CH_3)COOCH_3$
—$CH_2CH_2COOC_2H_5$
—$CH(CH_3)CH_2COOCH_3$
—$CH_2CH_2CH(CH_3)OCH_3$ —$CH_2$—(tetrahydrofuranyl, O)

—$(CH_2CH_2O)_2CH_3$
—$(CH_2CH_2O)_2C_2H_5$
—$(CH_2CH_2O)_2C_4H_9$
—$(CH_2CH_2O)_3CH_3$
—$(CH_2CH_2O)_3C_2H_5$
—$(CH_2CH_2O)_3C_{12}H_{25}$
—$(CH_2CH_2O)_5C_{10}H_{21}$
—$(CH_2CH_2O)_8C_9H_{19}$-bis-$C_{11}H_{23}$ (mixture)

—$(CH_2CH_2O)_{10}$—(phenyl)—$C_9H_{19}$

—$CH_2CH_2N(C_2H_5)_2$

—$CH_2CH_2$—N(morpholino, O)

—$CH_2CH_2$—N(piperidino)

-continued

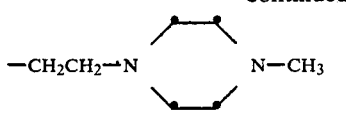

$R^{14} = CH_3, R^{13} = C_6H_{13}$
$R^{14} = CH_3, R^{13} = C_{10}H_{21}$
$R^{14} = CH_3, R^{13} = +CH_2CH_2O)_3-C_{12}H_{25}$ bis-$C_{15}H_{31}$ (mixture)
$R^{14} = CH_3, R^{13} = +CH_2CH_2O)_5-C_9H_{19}$ bis-$C_{11}H_{23}$ (mixture)

Examples of 4-aroyl-1,3-dioxolanes are:
4-benzoyl-2,2,4-trimethyl-1,3-dioxolane
4-benzoyl-4-methyl-2,2-tetramethylene-1,3-dioxolane
4-benzoyl-4-methyl-2,2-pentamethylene-1,3-dioxolane
cis-trans 4-benzoyl-2,4-dimethyl-2-methoxymethyl-1,3-dioxolane
cis-trans 4-benzoyl-4-methyl-2-phenyl-1,3-dioxolane
4-(4-methoxybenzoyl)-2,2,4-trimethyl-1,3-dioxolane
4-(4-methoxybenzoyl)-4-methyl-2,2-pentamethylene-1,3-dioxolane
4-(4-methylbenzoyl)-2,2,4-trimethyl-1,3-dioxolane
cis-trans 4-benzoyl-2-methyl-4-phenyl-1,3-dioxolane
4-benzoyl-2,2,4,5,5-pentamethyl-1,3-dioxolane
cis-trans 4-benzoyl-2,2,4,5-tetramethyl-1,3-dioxolane
cis-trans 4-benzoyl-4-methyl-2-pentyl-1,3-dioxolane
cis-trans 4-benzoyl-2-benzyl-2,4-dimethyl-1,3-dioxolane
cis-trans 4-benzoyl-2-(2-furyl)-4-methyl-1,3-dioxolane
cis-trans 4-benzoyl-5-phenyl-2,2,4-trimethyl-1,3-dioxolane
4-(4-methoxybenzoyl)-2,2,4,5,5-pentamethyl-1,3-dioxolane.

Examples of dialkoxyacetophenones are:
α,α-dimethoxyacetophenone
α,α-diethoxyacetophenone
α,α-diisopropoxyacetophenone
α,α-di-(2-methoxyethoxy)acetophenone
α-butoxy-α-ethoxyacetophenone
α,α-dibutoxy-4-chloroacetophenone
α,α-diethoxy-4-fluoroacetophenone
α,α-dimethoxy-4-methylacetophenone
α,α-diethoxy-4-methylacetophenone
α,α-dimethoxypropiophenone
α,α-diethoxypropiophenone
α,α-diethoxybutyrophenone
α,α-dimethoxyisovalerophenone
α,α-diethoxy-α-cyclohexylacetophenone
α,α-dipropoxy-4-chloropropiophenone.

Examples of α-hydroxy- and α-aminoacetophenones are:
2-hydroxy-2-methyl-1-phenyl-1-propanone
2-hydroxy-2-ethyl-1-phenyl-1-hexanone
1-(4-dodecylphenyl)-2-hydroxy-2-methyl-1-propanone
1-(2,4-dimethylphenyl)-2-hydroxy-2-methyl-1-propanone
2-hydroxy-1-(4-methoxyphenyl)-2-methyl-1-propanone
2-hydroxy-2-methyl-1-phenyl-1-butanone
2-dimethylamino-2-methyl-1-phenyl-1-propanone
2-dibutylamino-2-methyl-1-phenyl-1-propanone
1-(4-fluorophenyl)-2-methyl-2-morpholino-1-pentanone
2-methyl-1-(4-methylthiophenyl)-2-morpholino-1-propanone
2-dimethylamino-1-(4-methoxyphenyl)-2-methyl-1-propanone
2-diethylamino-1-(4-diethylaminophenyl)-2-methyl-1-propanone.

Examples of α-hydroxycycloalkyl phenyl ketones are:
α-hydroxycyclohexyl phenyl ketone
α-hydroxycyclopentyl phenyl ketone.

The photoinitiator mixture (b)+(c) can be added in amounts of from 0.5–20, preferably 1 to 10, % by weight, based on component (a).

The choice of solvent and concentration depends primarily on the nature of the composition and on the coating process. The composition is applied evenly to a substrate by means of known coating processes, for example by dipping, knife coating, curtain coating, electrophoresis, brushing-on, spraying or reverse-roll coating. The amount applied (coating thickness) and the nature of the substrate (coating base) depend on the desired field of application. For example, polyester or cellulose acetate films or plastic-coated papers are used as the coating base for photographic information recording; specially treated aluminium is used for offset printing plates, and copper-coated laminates are used for the production of printed circuits. The coating thicknesses for photographic materials and offset printing plates are generally about 0.5 to about 10 μm; for printed circuits generally about 1 to 100 μm. When solvents are also used, they are removed after coating.

Photocurable compositions, as are used for various purposes, usually contain a number of various additives in addition to the photopolymerizable compounds and the photoinitiators. Thus, it is frequently customary to add thermal inhibitors, which are intended to provide protection against premature polymerization, in particular during production of the compositions by mixing the components. For this hydroquinone, hydroquinone derivatives, p-methoxyphenol, β-naphthols or sterically hindered phenols, for example 2,6-di(tert-butyl)-p-cresol, for example, are used. Furthermore, small amounts of UV absorbers may be added, for example those of the benzotriazole, benzophenone or oxalanilide type. It is also possible to add light screens of the sterically hindered amine type (HALS).

In order to increase the shelf life in the dark, copper compounds, such as copper naphthenate, copper stearate or copper octanoate, phosphorus compounds, such as triphenylphosphine, tributylphosphine, triethyl phosphite, triphenyl phosphite or tribenzyl phosphite, quaternary ammonium compounds, such as tetramethylammonium chloride or trimethylbenzylammonium chloride, or hydroxylamine derivatives, for example N-diethylhydroxylamine, can be added.

In order to exclude the inhibiting action of atmospheric oxygen, paraffin or similar waxy substances are frequently added to photocurable mixtures. Due to their poor solubility in the polymer, these substances float out at the beginning of the polymerization and form a transparent surface layer which prevents entry of air.

Further customary additives are photosensitizers which absorb at certain wavelengths and pass on the absorbed energy to the initiators or themselves function as additional initiators. Examples of these are, in particular, thioxanthone, anthracene, anthraquinone and coumarine derivatives.

Further customary additives are accelerators of the amine type, which are particularly important in pigmented preparations since they act as chaintransfer agents. Examples of these are N-methyldiethanolamine, triethylamine, ethyl p-dimethylaminobenzoate or Michler's ketone. The action of the amines can be reinforced by adding aromatic ketones of the benzophenone type. Further customary accelerators are 1,3,4-thiadiazole derivatives, for example 2-mercapto-5-methylthio-1,3,4-thiadiazole.

Further customary additives are, for example, fillers, pigments, dyes, adhesives, wetting agents and flow-control agents.

Photocuring is of great importance in printing inks since the drying time of the binder is a prominent factor for the production rate of graphic products and should be in the order of magnitude of fractions of seconds. UV-curable printing inks are particularly important for screen printing.

The photocurable compositions according to the invention are also highly suitable for the production of printing plates, in particular flexographic printing plates. In this case, for example, mixtures of soluble, linear polyamides or of styrene-butadiene rubber with photopolymerizable monomers, for example acrylamides or acrylates, and a photoinitiator are used. Films and plates made from these systems are exposed via the negative (or positive) of the print master, and the uncured parts are subsequently eluted using a solvent.

A further field of application for photocuring is metal coating, for example in the painting of sheeting for tubes, cans or bottle caps, and the photocuring of plastic coatings, for example floor or wall coverings based on PVC.

Examples of the photocuring of paper coatings are the colourless coating of labels, record sleeves or book covers.

The use of the photocurable compositions for imaging processes and for optical production of information carriers is also important. Here, the layer (wet or dry) applied to the base is irradiated with shortwave light through a photomask, and the unexposed areas of the layer are removed by treatment with a solvent (=developer). The exposed areas are crosslinked polymeric and therefore insoluble and remain on the base. When dyed appropriately, visible images are produced. If the base is a metallized layer, the metal can be removed at the unexposed areas by etching after exposure and development or supplemented by electroplating. In this way, printed circuits and photoresists can be produced.

Light sources which are suitable for exposure are those having a high proportion of short-wave light. Today, appropriate technical equipment and various types of lamps are available for this purpose. Examples are carbon arc lamps, xenon arc lamps, mercury vapour lamps, metal-halide lamps, fluorescent lamps, argon lamps or photoflood lamps. Recently, laser light sources have also been used. These have the advantage that photomasks are not necessary; the controlled laser beam writes directly on the photocurable layer.

The titanocenes according to the invention can readily be mixed with the components of the photocurable compositions or are readily soluble in the composition, which makes it possible to achieve high photosensitivity. They are also relatively readily accessible since the lithium fluoroarylpyrroles as starting materials are obtainable by lithium/hydrogen exchange. Prior introduction of halogens into the fluoroarylpyrrole is therefore superfluous.

The examples which follow illustrate the invention in greater detail.

A) PREPARATION OF THE INTERMEDIATES (1-ARYLPYRROLES)

EXAMPLES 1-7

1 mol of 2,4-difluoroaniline and 1 mol of diketone (see Table 1) are refluxed for one hour in 1 litre of ethanol. When the reaction is complete (monitoring using thin-layer chromatography), the mixture is fully evacuated in vacuo, and the residue is recrystallized from hot ethanol. Further details are given in Table 1.

EXAMPLE 8

1 mol of the compound of Example 1 is formylated using $POCl_3/DMF$ [J. Chem. Soc., 1954, 3842]. The product obtained is reacted with $(phenyl)_3PCH(CH_3)_2^{\oplus}I^{\ominus}$/potassium butoxide in tetrahydrofuran as solvent. Further details are given in Table 1.

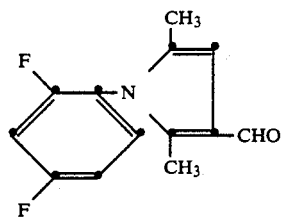

EXAMPLE 9

1 mol of the compound of Example 1 is reacted with $CF_3SO_3Si(CH_3)_3$ according to the procedure in Tetrahedron 42 (5), 1299 (1986). Further details are given in Table 1.

EXAMPLE 10

129 g of 2,4-difluoroaniline and 136.1 g of 2,5-dimethoxytetrahydrofuran are heated at 260° C. for 2 hours in an autoclave. After cooling, the reaction product is subjected to steam distillation. The distillate is extracted by shaking with petroleum ether, and the organic phase is separated off, dried using $Na_2SO_4$ and evaporated in vacuo. 167 g of a virtually colourless oil which crystallizes after standing for a short time are obtained. Further details are given in Table 1.

TABLE 1

| Example | Diketone | Product | Isolation/ purification | Yield (%) | Consistency | Melting/ boiling point (°C.) | Analysis (line 1: calculated, line 2: found) | | | | |
|---|---|---|---|---|---|---|---|---|---|---|---|
| | | | | | | | % C | % H | % F | % N | % O |
| 1 | [H₃C-C(=O)-CH₂-C(=O)-CH₃] | 2,6-dimethyl-1-(2,4-difluorophenyl)pyrrole structure | recrystallization from ethanol (−78° C.) | 80 | white needles | 68 | 69.50 69.54 | 5.35 5.35 | 18.34 18.12 | 6.76 6.78 | |
| 2 | [H₃C-CH(CH₃)-C(=O)-CH₂-C(=O)-CH₃] | structure with isopropyl substituent | chromatography SiO₂, hexane, recrystallization (−78° C.) | 66 | white crystals | 27 | 71.47 71.57 | 6.43 6.48 | 16.15 15.99 | 5.95 5.97 | |
| 3 | [H₃C-CH(propyl)-C(=O)-CH₂-C(=O)-CH₃ with CH₃] | structure with additional alkyl substituents | recrystallization from ethanol (−78° C.) | 55 | white powder | 43 | 74.20 74.02 | 7.96 8.08 | 13.04 13.03 | 4.81 4.79 | |

TABLE 1-continued

| Example | Product (starting) | Product | Isolation/purification | Yield (%) | Consistency | Melting/boiling point (°C.) | Analysis (line 1: calculated, line 2: found) | | | | |
|---|---|---|---|---|---|---|---|---|---|---|---|
| | | | | | | | % C | % H | % F | % N | % O |
| 4 | [structure: H3C-C(=O)-CH2-C(=O)-CH2-O-CH3] | [structure: 2,4-difluorophenyl pyrrole with CH3 and CH2OCH3 substituents] | chromatography SiO2/hexane, mix slowly with ether | 33 | yellowish oily liquid | — | 66.92 | 6.02 | 15.12 | 5.58 | 6.37 |
| | | | | | | | 66.37 | 6.03 | 16.65 | 6.13 | 4.82 |
| 5 | [structure: H3C-C(=O)-CH2-C(=O)-CH2-C6H5] | [structure: 2,4-difluorophenyl pyrrole with CH3 and C6H5 substituents] | recrystallization from ethanol | 82 | beige needles | 109 | 75.83 | 4.87 | 14.11 | 5.20 | |
| | | | | | | | 75.73 | 4.89 | 14.24 | 5.23 | |
| 6 | [structure: H3C-C(=O)-CH2-C(=O)-CH-furan] | [structure: 2,4-difluorophenyl pyrrole fused with furan] | chromatography SiO2/hexane | 90 | yellow crystals | 44 | 69.49 | 4.28 | 14.66 | 5.40 | 6.17 |
| | | | | | | | 69.66 | 4.43 | 14.52 | 5.37 | 6.02 |

TABLE 1-continued

| Example | Product | Educt | Isolation/ purification | Yield (%) | Consistency | Melting/ boiling point (°C.) | Analysis (line 1: calculated, line 2: found) | | | | |
|---|---|---|---|---|---|---|---|---|---|---|---|
| | | | | | | | % C | % H | % F | % N | % O |
| 7 | [structure] | [structure] | recrystallization from ethanol | 39 | yellowish crystals | 104 | 75.24 75.10 | 6.67 6.68 | 13.22 13.27 | 4.88 4.99 | — — |
| 8 | [structure] | [structure] Ph₃PCH(CH₃)₂⁺I⁻/KO-t-butyl | chromatography SiO₂/hexane:ether (1:1) | 82 | yellowish liquid | | 73.54 73.34 | 6.56 6.69 | 14.54 14.17 | 5.36 5.37 | Si |
| 9 | [structure] | [structure] CF₃SO₃Si(CH₃)₃ | ball-tube distillation | 65 | pale yellow liquid | 170 2 × 10⁻¹ mbar | 64.48 64.36 | 6.86 6.91 | 13.60 13.55 | 5.01 5.08 | 10.05 10.04 |

TABLE 1-continued

| Example | Product | Isolation/ purification | Yield (%) | Consistency | Melting/ boiling point (°C.) | Analysis (line 1: calculated, line 2: found) | | | |
|---|---|---|---|---|---|---|---|---|---|
| | | | | | | % C | % H | % F | % N | % O |
| 10 | [structure: H3CO, OCH3, O / 2,4-Difluoroaniline → N-aryl product with 2,4-difluorophenyl] | steam distillation | 93 | colourless crystals | 42 | 67.04 67.11 | 3.94 3.99 | 21.21 21.37 | 7.82 7.92 | — — |

EXAMPLE 11

A solution comprising 18 g of 40% strength dimethylamine in water (=0.16 mol of dimethylamine), 13.7 g of 35% strength formaline solution (=0.16 mol of formaldehyde) and 15 ml of glacial acetic acid is added dropwise to 0.1 mol of 1-(2,4-difluorophenyl)-2,5-dimethylpyrrole (product of Example 1). The resultant suspension is stirred at room temperature until the educt has reacted according to chromatographic analysis. The mixture is rendered basic using dilute sodium hydroxide solution, and the product is taken up in ether and washed with water. The crude product produced after concentration of the solution can be used as such for the next step or further purified by short-path distillation. Further details are given in Table 2.

EXAMPLES 12–21

The compounds were prepared by the process given for Example 11. The educts, mol-equivalents and reaction temperatures used are given in Table 2.

TABLE 2

| Example | Pyrrole | Amine (mol-equivalents of amine and $CH_2O$) Reaction temperature | Product | Yield | Analysis (line 1: calculated, line 2: found) | | |
|---|---|---|---|---|---|---|---|
| | | | | | % C | % H | % N |
| 11 | compound from Ex. 1 | $HN(CH_3)_2$ (1.6) RT | [structure] | 84% | 68.16 6.86 10.60 | | |
| | | | | | 67.83 6.91 10.55 | | |
| 12 | compound from Ex. 1 | $HN(CH_3)_2$ (3.2) 50° C. | [structure] | 88% | 67.26 7.84 13.07 | | |
| | | | | | 66.99 7.91 13.12 | | |
| 13 | compound from Ex. 1 | $HN(C_4H_9)(CH_3)$ (1.6) RT | [structure] | 99% | 70.56 7.90 9.14 | | |
| | | | | | 69.48 8.32 9.54 | | |
| 14 | compound from Ex. 1 | $HN(C_4H_9)_2$ (1.6) RT | [structure] | 53% | 72.38 8.68 8.04 | | |
| | | | | | 72.43 8.46 7.78 | | |
| 15 | compound from Ex. 1 | $HN(CH_2CH_2OCH_3)_2$ (1.6) RT | [structure] | 69% | 64.75 7.44 7.95 | | |
| | | | | | 64.34 7.52 7.86 | | |

TABLE 2-continued

| Example | Pyrrole | Amine (mol-equivalents of amine and CH₂O) Reaction temperature | Product | Yield | Analysis (line 1: calculated, line 2: found) % C | % H | % N |
|---|---|---|---|---|---|---|---|
| 16 | compound from Ex. 1 | HN⌒O (morpholine) (1.6) RT | 2,5-dimethyl-1-(2,4-difluorophenyl)-3-(morpholinomethyl)pyrrole | 45% | 66.65 66.44 | 6.58 6.51 | 9.14 8.96 |
| 17 | compound from Ex. 10 | HN(CH₃)₂ (3.2) 50° C. | 2,5-bis(dimethylaminomethyl)-1-(2,4-difluorophenyl)pyrrole | 76% | 65.51 65.51 | 7.22 7.15 | 14.32 14.07 |
| 18 | compound from Ex. 10 | HN(C₄H₉)(CH₃) (3.2) 50° C. | 2,5-bis[N-methyl-N-butylaminomethyl]-1-(2,4-difluorophenyl)pyrrole | 93% | 69.99 69.61 | 8.81 8.94 | 11.13 11.01 |
| 19 | compound from Ex. 10 | HN(C₄H₉)₂ (3.2) 50° C. | 2,5-bis(dibutylaminomethyl)-1-(2,4-difluorophenyl)pyrrole | 68% | 72.84 72.60 | 9.82 9.96 | 9.10 9.32 |
| 20 | compound from Ex. 10 | HN(CH₂CH₂OCH₃)₂ (3.2) 50° C. | 2,5-bis[N,N-bis(methoxyethyl)aminomethyl]-1-(2,4-difluorophenyl)pyrrole | 81% | 61.26 61.35 | 8.14 7.92 | 8.93 8.76 |
| 21 | compound from Ex. 10 | HN⌒O (morpholine) (3.2) 50° C. | 2,5-bis(morpholinomethyl)-1-(2,4-difluorophenyl)pyrrole | 95% | 63.38 63.65 | 7.02 6.68 | 11.36 11.13 |

Examples 22 and 23

0.05 mol of LiAlH₄ is added to 0.2 mol of the pyrrolaldehyde given in Table 3 (prepared by formylation of the corresponding pyrrole using POCl₃/DMF by the method of J. Chem. Soc. 1954, 3842) in 400 ml of dry diethyl ether, and the suspension is refluxed until educt can no longer be detected in the thin-layer chromatogram. After hydrolysis using aqueous MgSO₄ solution, the ether phase is dried and evaporated, the corresponding alcohol (hydroxymethylpyrrole) remaining. The latter is stirred with a suspension of 0.2 mol of NaH in 100 ml of dry diethyl ether until alcohol can no longer be detected in the thin-layer chromatogram. 0.3 mol of methyl iodide is then added, and the mixture is stirred overnight. After washing with water, the ether solution is dried and evaporated. The crude methoxymethylpyrrole is purified by column chromatography (silica gel/hexane/ethyl acetate). For further details, see Table 3.

Example 24

0.1 mol of the aminomethylpyrrole from Example 11 is dissolved in 20 ml of ethanol, and 0.1 mol of methyl iodide is added with cooling. After 30 minutes, the precipitated salt is filtered off, washed with ethanol and added to a solution of 0.14 mol of $C_2H_5ONa$ in ethanol. The suspension is refluxed for 4 days and then poured into water. The product is extracted with diethyl ether and purified by chromatography on silica gel (hexane/ethyl acetate 9:1). Further details are in Table 3.

evaporated, and the residue remaining is purified as stated in Table 5.

The products are yellow-orange to red-orange. The products are crystalline. All products are stable in the dark and are not sensitive to air.

In the tables below, Cp is cyclopentadienyl and Me is methyl. Chromatographic purification is carried out on columns with aluminium oxide (Woelm) neutral (=$Al_2O_3$) or silica gel 60 (Merck) (=$SiO_2$).

Example 36

44.7 g of N-2,4-difluorophenylpyrrole are dissolved in 750 ml of absolute diethyl ether, and the solution is cooled to $-75°$ C. 170 ml of a 15% strength hexane solution of butyllithium are added dropwise under $N_2$.

TABLE 3

| Example | Educt | Product | Yields (1st step/2nd step) | Analysis (line 1: calculated, line 2: found) % C | % H | % N |
|---|---|---|---|---|---|---|
| 22 | (structure) | (structure) | 78% / 56% | 66.92 / 67.02 | 6.02 / 5.99 | 5.57 / 5.62 |
| 23 | (structure) | (structure) | 88% / 37% | 64.57 / 64.51 | 4.97 / 5.19 | 6.27 / 6.07 |
| 24 | (structure) | (structure) | 11% | 67.91 / 67.82 | 6.46 / 6.47 | 5.28 / 5.13 |

B) PPREPARATION OF THE TITANOCENES

Examples 25–35

The amounts specified in each case in Table 4 of fluoroaromatic compound are dissolved under argon in the particular solvent, the appropriate amount of 1.6 molar butyllithium/hexane solution is added dropwise at $-70°$ C., and the mixture is stirred at $-70°$ C. for a further one hour. The stated amount of titanocene dichloride is subsequently added in one portion, and the reaction mixture is warmed slowly to room temperature and stirred at room temperature for a further three hours. The mixture is then fully evaporated in vacuo, the residue is extracted with dichloromethane or chloroform, and the extracts are filtered. The filtrate is re- After stirring for 1 hour at $-75°$ C., 31.1 g of titanocene dichloride are added. After removal of the cooling and when room temperature is reached, the orange suspension is taken up in 2 l of ethyl acetate, and the solution is washed 3x with $H_2O$, dried using $Na_2SO_4$ and evaporated on a rotary evaporator. 73.5 g of an orange resin are obtained.

The orange resin is stirred overnight with 250 ml of ethanol, during which time crystallization commences. After filtration and washing with a little ethanol, 53.7 g of pale orange crystals of melting point 165°–166° C., are obtained, yield 80.4%. For analysis, the product can be recrystallized from ethanol.

Examples 37–42

The procedure followed was as in Examples 25–35. Further details are given in Tables 4 and 5.

TABLE 4

| Example | Titanium compound/amount | Fluoroaromatic of example/amount | Butyllithium 1.6 M in hexane | Solvent |
|---|---|---|---|---|
| 25 | cp$_2$TiCl$_2$/6,5 g | 1: 10.4 g | 31.25 ml | THF 250 ml |
| 26 | (Me$_3$Sicp)$_2$ TiCl$_2$/10,2 g | 1: 10.4 g | 31.25 ml | THF 250 ml |
| 27 | (Me cp)$_2$ TiCl$_2$/7,2 g | 1: 10.4 g | 31.25 ml | THF 250 ml |
| 28 | cp$_2$ TiCl$_2$/4,8 g | 2: 8.7 g | 23.1 ml | THF 250 ml |
| 29 | cp$_2$ TiCl$_2$/2,5 g | 3: 5.8 g | 12.5 ml | THF 140 ml |
| 30 | cp$_2$ TiCl$_2$/2,0 g | 4: 4.0 g | 10 ml | THF 110 ml |
| 31 | cp$_2$ TiCl$_2$/7,7 g | 5: 16.2 g | 37.5 ml | THF 400 ml |
| 32 | cp$_2$ TiCl$_2$/2,2 g | 6: 4.5 g | 10.9 ml | THF 120 ml |
| 33 | cp$_2$ TiCl$_2$/4,2 g | 7: 9.2 g | 20.05 ml | THF 200 ml |
| 34 | cp$_2$ TiCl$_2$/2,4 g | 8: 5.0 g | 12.0 ml | THF 100 ml |
| 35 | cp$_2$ TiCl$_2$/6,0 g | 9: 13.0 g | 29.1 ml | THF 300 ml |
| 37 | cp$_2$ TiCl$_2$/1,9 g | 11: 4.0 g | 20.0 ml | THF 40 ml |
| 38 | cp$_2$ TiCl$_2$/3,7 3,7 g | 12: 10.4 g | 20.3 ml | THF 220 ml |
| 39 | cp$_2$ TiCl$_2$/3,7 3,7 g | 15: 11.4 g | 20.3 ml | THF 220 ml |
| 40 | cp$_2$ TiCl$_2$/1,9 g | 16: 4.6 g | 10.0 ml | THF 40 ml |
| 41 | cp$_2$ TiCl$_2$/3,7 g | 17: 9.5 g | 20.3 ml | THF 220 ml |
| 42 | cp$_2$ TiCl$_2$/1,9 g | 21: 5.1 g | 10.0 ml | THF 40 ml |

TABLE 5

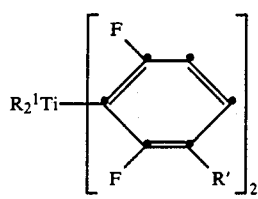

| Example | R$^1$ | R' | Purification | Melting point (°C.) |
|---|---|---|---|---|
| 25 | Cp | 2,5-dimethylpyrrolyl | Recrystallization from diethyl ether/hexane | 205 (decomposition) |
| 26 | Me$_3$SiCp | 2,5-dimethylpyrrolyl | Washing with pentane | 113 |
| 27 | MeCp | 2,5-dimethylpyrrolyl | Washing with pentane | 106 |
| 28 | Cp | 2-methyl-5-isopropylpyrrolyl | Chromatography: hexane; hexane/diethyl ether | 197 |
| 29 | Cp | 2-methyl-5-butylpyrrolyl | Chromatography as Example 28 | 74 |

TABLE 5-continued $$\left[ R_2{}^1 Ti - \begin{array}{c} F \\ \\ F \end{array} \begin{array}{c} \\ \\ R' \end{array} \right]_2$$

| Example | R¹ | R' | Purification | Melting point (°C.) |
|---------|-----|-----|--------------|---------------------|
| 30 | Cp | 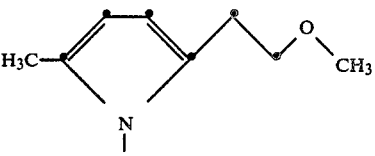 | Chromatography: hexane/ether | 72 |
| 31 | Cp | 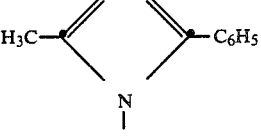 | Recrystallization from diethyl ether/ pentane | 200 |
| 32 | Cp | 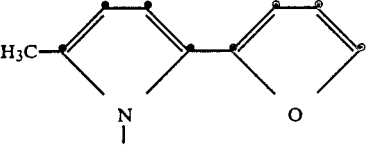 | Recrystallization from 1. Hexane 2. Diethyl ether | 203 |
| 33 | Cp | 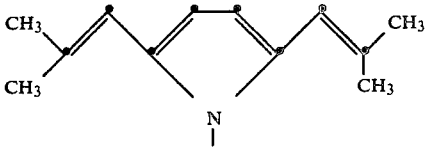 | Chromatography as Example 28, recrystallization from diethyl ether/pentane | decomposition >100 |
| 34 | Cp | 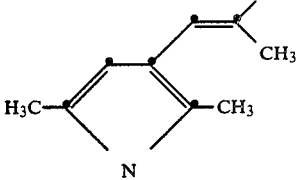 | Recrystallization from diethyl ether | decomposition >100 |
| 35 | Cp | 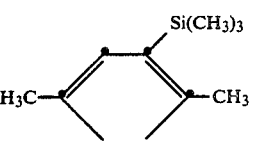 | Washing with hexane | 130 |
| 36 | Cp | 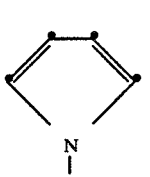 | Recrystallization from ethanol | 165 |

TABLE 5-continued

[Structure: R₂¹Ti— bonded to a cyclohexadiene ring with F, F, and R' substituents, shown as ]₂]

| Example | R¹ | R' | Purification | Melting point (°C.) |
|---|---|---|---|---|
| 37 | Cp | [pyrrole ring with CH₃, CH₃, N(CH₃)₂ substituents and N-H] | Recrystallization from CH₂Cl₂/hexane | 75–80 |
| 38 | Cp | [pyrrole ring with CH₃N(CH₃)CH₂—, CH₃, CH₃, —CH₂N(CH₃)₂ substituents and N-H] | Extraction with H₂O; recrystallization from hexane | 108 |
| 39 | Cp | [pyrrole ring with CH₃, CH₃, N(CH₂CH₂OCH₃)₂ substituents and N-H] | Washing with hexane, recrystallization from CH₂Cl₂/hexane | from 70 |
| 40 | Cp | [pyrrole ring with CH₃, CH₃, morpholinyl substituents and N-H] | Washing with hexane; recrystallization from CH₂Cl₂/hexane | 197–200 |
| 41 | Cp | [pyrrole ring with (CH₃)₂NCH₂— and —CH₂N(CH₃)₂ substituents and N-H] | Recrystallization from CH₂Cl₂/hexane | 175 |
| 42 | Cp | [pyrrole ring with morpholinylmethyl groups on both sides and N-H] | Chromatography, recrystallization from CH₂Cl₂/hexane | 100–105 |

TABLE 5-continued

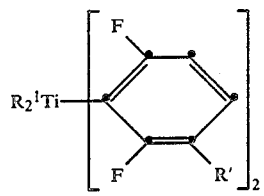

| Example | R¹ | R' | Purification | Melting point (°C.) |
|---|---|---|---|---|
| 43 | MeCp | (pyrrole-diyl structure) | Chromatography ethyl acetate/ hexane | 85° |

C) USE EXAMPLES

Example 44

Photocuring of an acrylate mixture. A photocurable composition is produced by mixing the following components:

| | | Solids content |
|---|---|---|
| 150.30 g of Scripset 540[1] (30% strength solution in acetone) | 45.1 g | |
| 48.30 g of trimethylolpropane triacrylate | 48.3 g | |
| 6.60 g of polyethylene glycol diacrylate | 6.6 g | |
| 0.08 g of Crystal Violet | | |
| 205.28 g | 100.0 g | |

[1]Polystyrene-maleic anhydride copolymer (Monsanto)

Portions of this composition are mixed with the amount stated in the table below of photoinitiator or initiator mixtures. The initiator mixtures are solutions of a titanocene in a liquid initiator comprising a 1:1 mixture of α-hydroxycyclohexyl phenyl ketone and benzophenone. All operations are carried out under red or yellow light.

The samples mixed with initiator are applied to 200 μm aluminium foil (10×15 cm) in a thickness of 150 μm. The solvent is removed by warming for 15 minutes at 60° C. in a circulation oven. A polyester film of thickness 76 μm is placed on the liquid layer, and a standardized test negative with 21 steps of various optical density (Stauffer wedge) is placed on the latter. A second polyester film is placed on top, and the laminate obtained in this way is fixed on a metal plate. The sample is then exposed using a 5 kW metal-halide lamp at a distance of 30 cm, for 20 seconds in a first test series and for 40 seconds in a second test series. After exposure, the films and mask are removed, and the exposed layer is developed in an ultrasound bath for 120 seconds using developer A and subsequently dried for 15 minutes at 60° C. in a circulation oven. The sensitivity of the initiator system used is characterized by specifying the final wedge step which has been imaged without adhesion. The higher the number of steps, the more sensitive the system. An increase by two steps here indicates a doubling of the curing rate.

The results are given in Table 6. Developer A contains 15 g of sodium metasilicate.9 $H_2O$; 0.16 g of KOH; 3 g of polyethylene glycol 6000; 0.5 g of levulinic acid and 1000 g of demineralized water.

TABLE 6

| Amount of photoinitiator* | | Number of imaged steps | |
|---|---|---|---|
| Titanocene of Example | Initiator | after 20 s | after 40 s exposure |
| 0.3% of 28 | — | 17 | 19 |
| 0.3% of 28 | 1.7% | 18 | 20 |
| 0.3% of 29 | — | 14 | 16 |
| 0.3% of 29 | 1.7% | 15 | 18 |
| 0.3% of 31 | — | 14 | 16 |
| 0.3% of 31 | 1.7% | 16 | 18 |
| 0.3% of 34 | 1.7% | 16 | 18 |
| 0.3% of 34 | 1.7% | 17 | 19 |
| 0.3% of 30 | — | 15 | 17 |
| 0.3% of 32 | — | 11 | 13 |
| 0.3% of 33 | — | 13 | 15 |
| 0.3% of 35 | — | 14 | 16 |
| 0.3% of 25 | — | 16 | 20 |
| 0.3% of 26 | — | 13 | 16 |
| 0.3% of 36 | — | 15 | 18 |
| 0.3% of 43 | — | 12 | 14 |
| 0.2% of 25 | — | 15 | 17 |
| 0.2% of 26 | — | 11 | 13 |
| 0.2% of 27 | — | 10 | 12 |

*based on the photocurable composition

Example 45

Photocuring of an acrylate mixture

A photocurable composition is produced by mixing the following components:

| 37.64 g | of Sartomer SR 444 | (Pentaerythritol triacrylate) (Sartomer Company, Westchester) |
|---|---|---|
| 10.76 g | of Cymel 301 | Hexamethoxymethylmelamine (Cyanamid) |
| 47.30 g | of Carboset 525 | (Thermoplastic acrylate containing carboxyl groups/B. F. Goodrich) |
| 4.30 g | of polyvinylpyrrolidone PVP (GAF) | |
| 100.00 g | of the above mixture | |
| 0.50 g | of Irgalit green GLN | |
| 319.00 g | of methylene chloride | |
| 30.00 g | of methanol | |

450.00 g

Portions of this composition are mixed with the amounts stated in the table below of titanocene. All operations are carried out under a red or yellow light.

The samples mixed with initiator are applied to 200 μm aluminium foil (10×15 cm) in a thickness of 200 μm. The solvent is removed by warming at 60° C. for 15 minutes in a circulation oven. A polyester film of thickness 76 μm is placed on the liquid layer, and a standardized test negative containing 21 steps of various optical density (Stauffer wedge) is placed on the film. A second polyester film is placed on top, and the laminate obtained in this way is fixed on a metal plate. The sample is then exposed using a 5 kW metal-halide lamp at a distance of 30 cm, for 20 seconds in a first test series and for 40 seconds in a second test series. After exposure, the films and masks are removed, and the exposed layer is developed in an ultrasound bath for 240 seconds using developer A and subsequently dried at 60° C. for 15 minutes in a circulation oven. The sensitivity of the initiator system used is characterized by specifying the final wedge step imaged without adhesion. The higher the number of steps, the more sensitive the system. An increase by two steps indicates here a doubling of the curing rate. The results are given in Table 7.

TABLE 7

| Amount of titanocene* | Number of imaged steps | |
|---|---|---|
| of Example | After 20 s | After 40 s exposure |
| 0.3% of 28 | 13 | 15 |
| 0.3% of 29 | 12 | 15 |
| 0.3% of 30 | 11 | 14 |
| 0.3% of 31 | 12 | 14 |
| 0.3% of 32 | 10 | 13 |
| 0.3% of 33 | 10 | 13 |
| 0.3% of 34 | 11 | 13 |
| 0.3% of 35 | 12 | 14 |
| 0.3% of 25 | 13 | 16 |
| 0.3% of 36 | 15 | 17 |
| 0.3% of 39 | 8 | 10 |
| 0.3% of 42 | 7 | 10 |
| 0.3% of 43 | 13 | 15 |

*based on the solvent-free photocurable composition

What is claimed is:

1. A titanocene of the formula 1

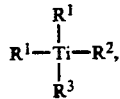 (I)

in which both $R^1$ radicals, independently of one another, are cyclopentadienyl⊖, indenyl⊖ or 4,5,6,7-tetrahydroindenyl⊖, each of which is unsubstituted or mono- or polysubstituted by $C_1$-$C_{18}$alkyl or -alkoxy, $C_2$-$C_{18}$alkenyl, $C_5$-$C_8$cycloalkyl, $C_6$-$C_{16}$aryl, $C_7$-$C_{16}$aralkyl, $SiR_3^4$, $GeR_3^4$, cyano or halogen, or both $R^1$ together are a radical of the formula II

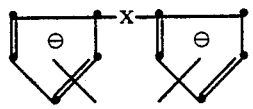 (II)

unsubstituted or substituted as above, in which X is —$CH_2$—n where n=1, 2 or 3, unsubstituted or phenyl-substituted alkylidene having 2 to 12 carbon atoms, cycloalklidene having 5 to 7 ring carbon atoms, $SiR_2^4$, $SiR_2^4$—O—$SiR_2^4$, $GeR_2^4$ or $SnR_2^4$, and $R^4$ is $C_1$-$C_{12}$alkyl, $C_5$-$C_{12}$cycloalkyl, $C_6$-$C_{16}$aryl or $C_7$-$C_{16}$aralkyl, $R^2$ is a 6-membered carbocyclic or 5- or 6-membered heterocyclic aromatic ring which is substituted by fluorine atoms in at least one of the two ortho-positions to the titanium-carbon bond, and in which the aromatic ring may contain further substituents, $R^3$, independently, is as defined for $R^2$ or $R^2$ and $R^3$ together are a radical of the formula III

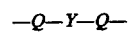 (III)

in which Q is a carbocyclic aromatic ring where the two bonds are each in the ortho-position to the Y group and the second ortho-position to the titanium-carbon bond is in each case substituted by a fluorine atom and where Q may contain further substituents, and Y is $CH_2$, alkylidene having 2 to 12 carbon atoms, cycloalkylidene having 5 to 7 ring carbon atoms, $NR^4$, O, S, SO, $SO_2$, CO, $SiR_2^4$, $GeR_2^4$ or $SnR_2^4$, and $R^4$ is as defined above, wherein, in the titanocenes, $R^2$ and $R^3$ are substituted by a radical of the formula IV

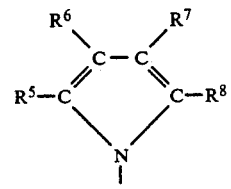 (IV)

in which $R^5$, $R^6$, $R^7$ and $R^8$, independently of one another, are a hydrogen atom, linear or branched $C_1$-$C_{18}$alkyl, $C_2$-$C_5$alkenyl, $C_7$-$C_9$aralkyl or -alkaryl, $C_8$-$C_{10}$alkaralkyl, $C_6$-$C_{10}$aryl, 2-furyl, $C_5$-$C_8$cycloalkyl, $C_5$-$C_8$cycloalkenyl, $C_2$-$C_{12}$alkanoyl or $C_2$-$C_{12}$alkoxycarbonyl each of which is unsubstituted or substituted by $C_2$-$C_8$dialkylamino or -aminomethyl, bis-[2-($C_1$-$C_4$alkoxy)ethyl]-amino or -aminomethyl, morpholino, morpholinylmethyl, piperidino, piperidinylmethyl, N-methylpiperazino, N-methylpiperazinylmethyl, pyrrolidino, pyrrolidinylmethyl, quaternary $C_3$-$C_{10}$trialkylammonium or -ammoniummethyl, $C_1$-$C_{12}$alkoxy, —O$CH_2CH_2$)$_1$0-$C_1$-$C_{16}$alkyl in which 1 is a number from 1 to 20, 1,3-dioxolan-2-yl, 4-methyl-1,3-dioxolan-2-yl, —O$CH_2CH_2$O—, $C_1$-$C_{12}$alkoxycarbonyl, $C_2$-$C_{12}$alkanoyloxy, $C_2$-$C_{12}$alkanoyl, $C_1$-$C_{12}$alkylthio, halogen, cyano or $SiR_3^4$ in which $R^4$ is as defined above; or are —CHO, —$SiR_3^4$ or —$GeR_3^4$ in which $R^4$ is as defined above; or $R^5$ and $R^6$ and/or $R^7$ and $R^8$ or $R^6$ and $R^7$ in each case together are —($CH_2$)$_3$—, —($CH_2$)$_4$—, —CH=CH—CH=CH—, —CH=CH—C($R^{11}$)=CR—, —$CH_2OCH_2$— or —$CH_2N(C_1$-$C_4$alkyl)$CH_2$— in which $R^{11}$ is hydroxyl, $C_1$-$C_4$alkoxy or $C_2$-$C_4$alkanoyloxy.

2. A titanocene according to claim 1, wherein $R^1$ is cyclopentadienyl⊖ or methylcyclopentadienyl⊖.

3. A titanocene according to claim 1, wherein $R^2$ and $R^3$ are identical.

4. A titanocene according to claim 1, wherein the $R^2$ radical is substituted by fluorine in both ortho-positions to the titanium-carbon bond.

5. A titanocene according to claim 1, wherein $R^2$ and $R^3$ are 2,6-difluorophen-1-yl to which a radical of the formula IV is bound, and which may contain a further 1 or 2 identical or different substituents.

6. A titanocene according to claim 5, wherein, in the formula I, both $R^1$ are cyclopentadienyl$\ominus$ or $C_1$–$C_4$alkyl-substituted cyclopentadienyl$\ominus$, and $R^2$ and $R^3$ are radicals of the formula V

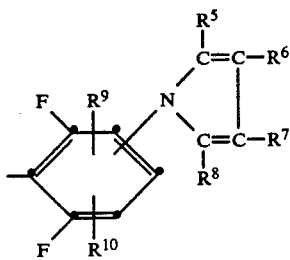
 (V)

in which $R^5$, $R^6$, $R^7$ and $R^8$ are as defined in claim 1, and $R^9$ and $R^{10}$, independently of one another, are H or F.

7. A titanocene according to claim 6, wherein, in the formula V, the pyrrole group is bound in the ortho-position to an F atom.

8. A titanocene according to claim 6, wherein $R^9$ and $R^{10}$ are H.

9. A titanocene according to claim 1, wherein $R^5$, $R^6$, $R^7$ and $R^8$, independently of one another, are a hydrogen atom or unsubstituted or substituted $C_1$–$C_{12}$alkyl, $C_2$–$C_5$alkenyl, $C_7$- or $C_8$aralkyl or -alkaryl, phenyl, 2-furyl, $C_5$- or $C_6$cycloalkyl, $C_5$- or $C_6$cycloalkenyl, $C_2$–$C_8$alkanoyl or $C_2$–$C_5$alkoxycarbonyl; or are —CHO or $SiR_3^4$ in which $R^4$ is $C_1$–$C_8$alkyl.

10. A titanocene according to claim 9, wherein $R^5$, $R^6$, $R^7$ and $R^8$, independently of one another, are a hydrogen atom, or unsubstituted or substituted $C_1$–$C_8$alkyl, $C_2$–$C_4$alkenyl, benzyl, phenyl, 2-furyl, $C_5$- or $C_6$cycloalkyl, $C_2$–$C_6$alkanoyl or $C_2$–$C_5$alkoxycarbonyl; or are —CHO or $SiR_3^4$ in which $R^4$ is $C_1$–$C_4$alkyl.

11. A titanocene according to claim 9, wherein $R^5$, $R^6$, $R^7$ and $R^8$, independently of one another, are a hydrogen atom or unsubstituted or substituted $C_1$–$C_8$alkyl, $C_2$–$C_4$alkenyl, phenyl or 2-furyl or are $SiR_3^4$ in which $R^4$ is $C_1$–$C_4$alkyl.

12. A titanocene according to claim 1, wherein, in the formula IV, $R^6$ or $R^6$ and $R^7$ are H.

13. A process for the preparation of a titanocene of the formula I according to claim 1, wherein 1 mole of a compound of the formula VI

 (VI)

in which $R^1$ is as defined in claim 1 and Z is halogen, particularly chlorine, is reacted with one mole of $LiR^2$ and with one mole of $LiR^3$ or with 1 mole of $Li_2QYQ$, where $R^2$, $R^3$ and QYQ are as defined in claim 1, and the compound of the formula I is then isolated in a manner known per se.

14. A radiation-polymerizable composition, containing (a) at least one non-volatile, monomeric, oligomeric or polymeric compound containing at least one polymerizable, ethylenically unsaturated double bond, and (b) at least one titanocene of the formula I according to claim 1 as photoinitiator.

15. A composition according to claim 14, wherein, in addition, at least one photoinitiator (c) other than (b) is present.

16. A composition according to claim 15 which contains, as photoinitiator (c), a benzoin alkyl ether, a benzophenone, a benzil ketal, a 4-aroyl-1,3-dioxolane, a dialkoxyacetophenone, an α-hydroxy- or α-aminoacetophenone or an α-hydroxycycloalkyl phenyl ketone, or a mixture thereof, as an additional photoinitiator.

17. A method of photopolymerizing a non-volatile, monomeric, oligomeric or polymeric compound containing at least one polymerizable, ethylenically unsaturated double bond, which comprises adding an effective photoinitiating amount of at least one titanocene of formula I according to claim 1 to said compound, and irradiating the composition obtained.

18. A method according to claim 17 wherein at least one additional photoinitiator is also added.

19. A method according to claim 18 wherein the additional photoinitiator is selected from the group consisting of a benzoin alkyl ether, a benzophenone, a benzil ketal, a 4-aroyl-1,3-dioxolane, a dialkoxyacetophenone, an α-hydroxyacetophenone, an α-aminoacetophenone and an α-hydroxycycloalkyl phenyl ketone.

20. A substrate coated on at least one surface with a composition according to claim 14.

21. A photoinitiator mixture which contains a photoinitiator of the benzoin alkyl ether, benzophenone, benzil ketal, 4-aryl-1,3-dioxolane, dialkoxyacetophenone, α-hydroxyacetophenone, α-hydroxycycloalkyl phenyl ketone, α-aminoacetophenone type or a mixture thereof and a titanocene of the formula I according to claim 1.

* * * * *